(12) United States Patent
Bremer et al.

(10) Patent No.: US 7,712,385 B2
(45) Date of Patent: May 11, 2010

(54) METHOD FOR THE PREPARATION OF SAMPLES FOR AN ANALYZER AND SAMPLING STATION THEREFOR

(75) Inventors: Ralf Bremer, Oberhausen (DE); Bernhard Rose, Düsseldorf (DE)

(73) Assignee: Gerstel Systemtechnik GmbH & Co.KG (DE)

( * ) Notice: Subject to any disclaimer, the term of this patent is extended or adjusted under 35 U.S.C. 154(b) by 579 days.

(21) Appl. No.: 11/608,679

(22) Filed: Dec. 8, 2006

(65) Prior Publication Data

US 2007/0137320 A1 Jun. 21, 2007

(30) Foreign Application Priority Data

Dec. 15, 2005 (DE) ........................ 10 2005 060 291

(51) Int. Cl.
*G01N 1/00* (2006.01)
(52) U.S. Cl. .................................. 73/864.24
(58) Field of Classification Search ........................ None
See application file for complete search history.

(56) References Cited

U.S. PATENT DOCUMENTS

| | | | |
|---|---|---|---|
| 4,199,988 A | 4/1980 | Riegger | |
| 5,441,700 A | 8/1995 | Markelov | |
| 5,686,656 A * | 11/1997 | Amirav et al. | 73/23.41 |
| 5,756,905 A * | 5/1998 | Ueda | 73/864.24 |
| 5,792,423 A | 8/1998 | Markelov | |
| 5,932,482 A | 8/1999 | Markelov | |
| 6,277,649 B1 | 8/2001 | Markelov | |
| 6,360,794 B1 * | 3/2002 | Turner | 141/329 |
| 6,365,107 B1 | 4/2002 | Markelov et al. | |
| 6,395,229 B1 | 5/2002 | Markelov | |
| 6,395,560 B1 | 5/2002 | Markelov | |
| 6,974,495 B2 * | 12/2005 | Tipler et al. | 96/105 |
| 2005/0014156 A1 | 1/2005 | Pawliszyn | |
| 2005/0229723 A1 | 10/2005 | Bremer et al. | |
| 2006/0123883 A1 * | 6/2006 | Miyagawa | 73/23.37 |
| 2007/0137320 A1 | 6/2007 | Bremer et al. | |

FOREIGN PATENT DOCUMENTS

| | | |
|---|---|---|
| DE | 69504635T T2 | 5/1999 |
| DE | 10219790 C1 | 10/2003 |
| DE | 60011685 D | 7/2004 |
| DE | 11200500310 T | 3/2007 |

OTHER PUBLICATIONS

Hino et al., "Development of a whole headspace injection method for the determination of volatile organic compounds in water," Journal of Chromatography (1996) 746:83-90.

(Continued)

*Primary Examiner*—Robert R Raevis
(74) *Attorney, Agent, or Firm*—Townsend and Townsend and Crew LLP; Kenneth R. Allen

(57) ABSTRACT

A method for the preparation of samples for an analyzer and a sampling station therefor are provided which allow automated injection of larger inert-gas volumes to be introduced into a sample container via a packing, in order to enrich the packing of the substances of a sample to be investigated.

22 Claims, 6 Drawing Sheets

OTHER PUBLICATIONS

Hino et al., "Large Volume Injection by Headspace Purge with Trap Technique for CGC," Eighteenth International Symposium on Capillary Chromatography vol. 1, (May 20-24, 1996) pp. 609-616.

Maeda et al., "Dynamic Headspace Analysis. Application to Food Analysis," Eighteenth International Symposium on Capillary Chromatography (Eds. Sandra and Devos) vol. 1, (May 20-24, 1996) pp. 1096-1100.

* cited by examiner

METHOD FOR THE PREPARATION OF SAMPLES FOR AN ANALYZER AND SAMPLING STATION THEREFOR

CROSS-REFERENCES TO RELATED APPLICATIONS

See Application Data Sheet

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The invention relates to a method for the preparation of samples for an analyzer and to a sampling station therefor.

DE 102 19 790 C1 discloses a handling device for samples for an analyzer, the said handling device comprising a gripper which is movable along three axes perpendicular to one another and by means of which different samplers, such as, for example, different syringes or sample tubes equipped with transporting heads, can be handled. Syringes have a specific volume which is drawn up as a result of the movement of their piston. Thus, because of this, only a predetermined volume can be taken up from a sample container, the septum of which is pierced by means of the syringe needle. It is thus not possible by means of this handling device to direct larger volumes via a packing, in order to enrich on the packing the substances of a sample which are to be investigated.

BRIEF SUMMARY OF THE INVENTION

According to the invention, a method for the preparation of samples for an analyzer and a sampling station therefor are provided which allow automated injection of larger inert-gas volumes to be introduced into a sample container via a packing, in order to enrich the packing of the substances of a sample to be investigated.

According to a specific embodiment of the invention, a method for the preparation of samples for an analyzer comprises a sample container provided with a septum being brought into an extraction position of a sampling station comprising a sampler, the sampler being arranged above the sample container in an extraction position, the sampler comprising, for a sample tube, a reception tube movable in the direction of the sample container and detainable in an end position in a holder, a syringe needle, which terminates in the reception tube being movable by means of the reception tube, a sample tube open on both sides, in which a packing for the uptake of analytes is arranged, being inserted into the reception tube and, together with the latter, being moved within the holder in the direction of the sample container and detained, with the septum being pierced by the needle, an inert-gas stream being led from an inert-gas source through the sample container, the needle and the packing in the sample tube, and the sample tube, together with the packing laden with analytes, being removed from the reception tube.

Further according to the invention, a sampling station for the preparation of samples for an analyzer, in particular a chromatograph, from a sample container provided with a septum, comprises a container holder, arranged in an extraction position, for a sample container, a sampler with a holder, movable over a sample container in the extraction position, for a reception tube for a sample tube open on both sides, with a packing for the uptake of analytes, the reception tube being introducible and detainable in the holder and carrying a taken-along syringe needle which opens out inside the reception tube so as to project out of the latter.

Further embodiments of the invention may be gathered from the following description and the dependent claims.

The invention is explained in more detail below with reference to exemplary embodiments illustrated in the accompanying figures.

DETAILED DESCRIPTION OF THE INVENTION

Figure 1:
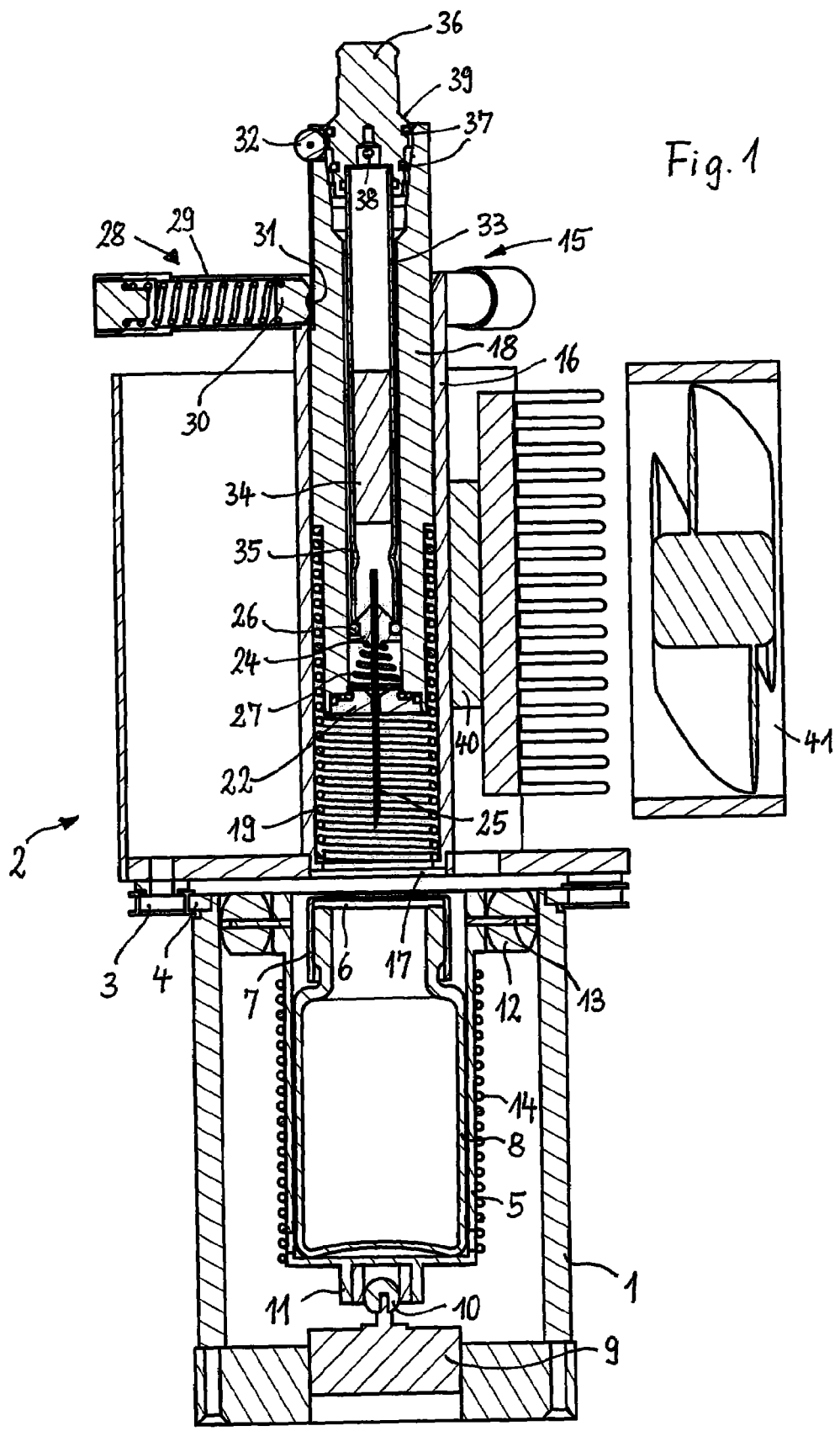
FIG. 1 shows an embodiment of a sampling station in cross-sectional view in the form of a detail.
Figure 2:
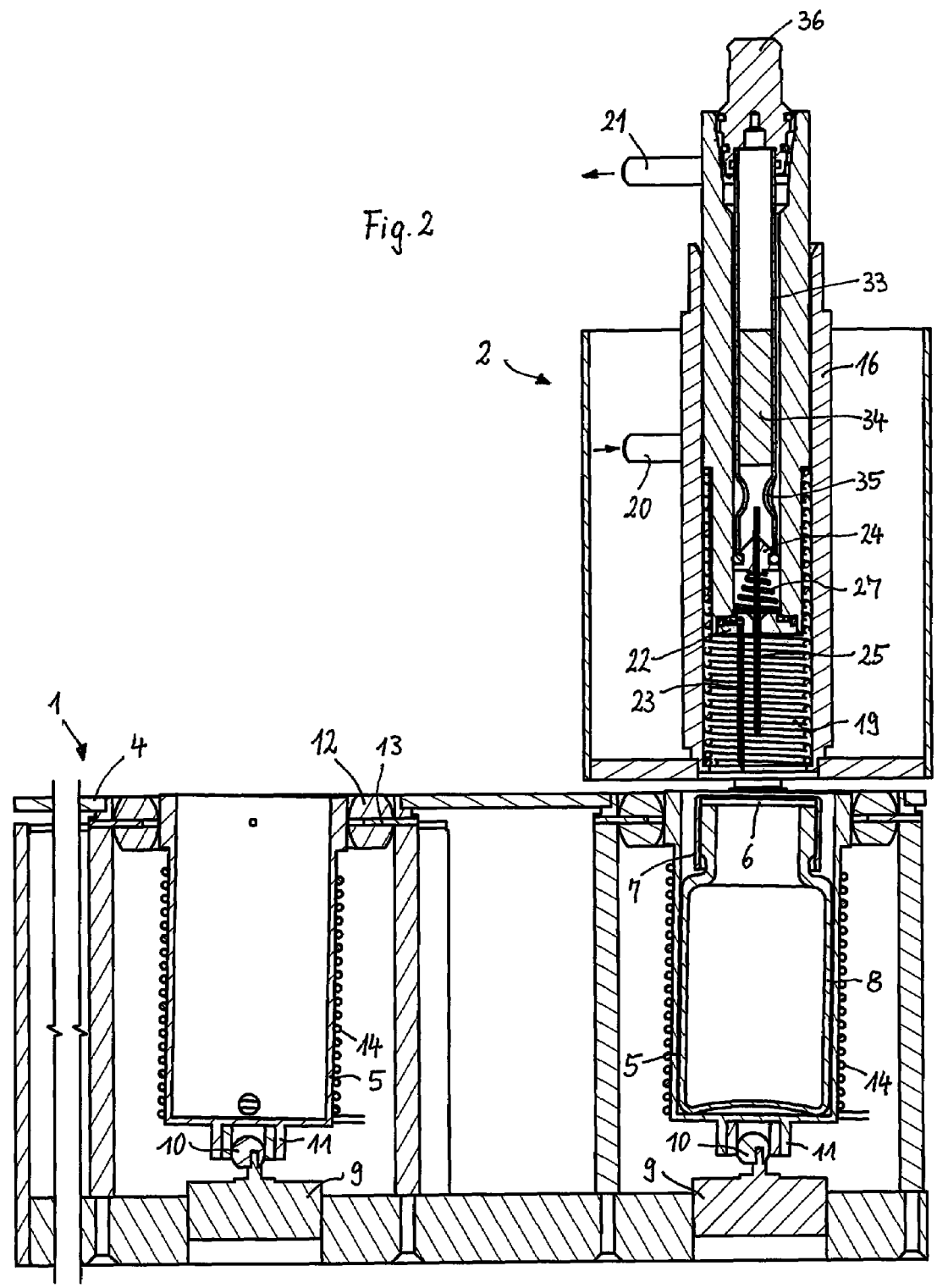
FIG. 2 shows in the form of a detail a cross-sectional view, rotated at 90°, through the sampling station of FIG. 1.
Figure 3:
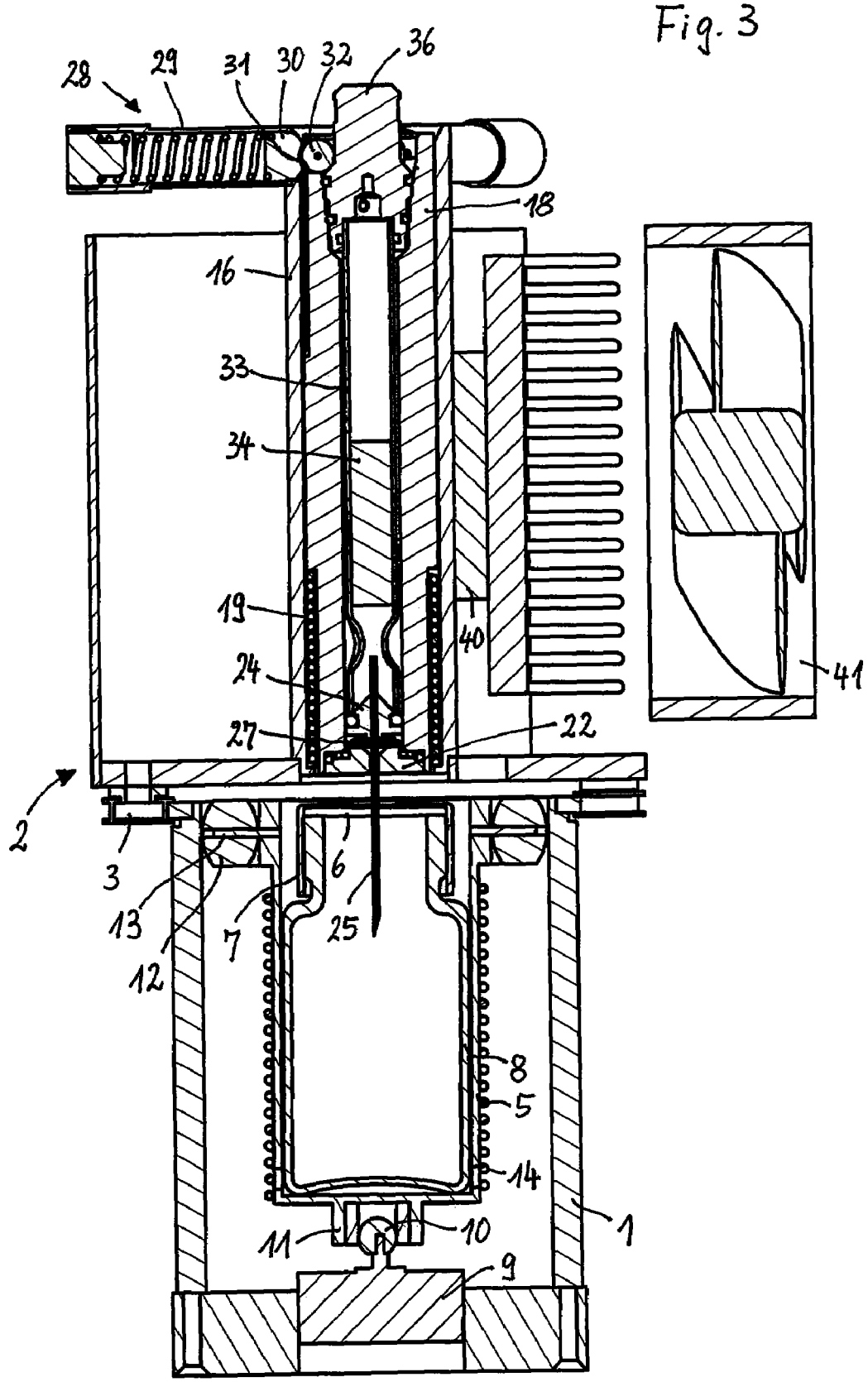
FIG. 3 shows the detail of FIG. 1 during sampling.

The sampling station illustrated in FIGS. 1 to 3 comprises a mount or stand 1 with a slide-shaped sampler 2 which is movable (or pivotable, not illustrated) via rollers 3 along rails 4 between two sampling positions. In each case one of these is used temporarily as a preparation position and the other as an extraction position. Located in each case in the sampling positions is a trough-like container holder 5 for receiving a sample container 8, in this exemplary embodiment a vial, provided with a cap 7 holding a septum 6.

Expediently, it is provided that the sample located in the respective sample container 8 can be shaken in the sampling positions.

For this purpose, for liquid samples, it may be provided that the sample container 8 contains a magnetic stirring element, whilst, in the respective sampling positions, in each case a device generating an alternating magnetic field is arranged below the container holder 5 in order to generate a stirring movement of the stirring element. Agitation or stirring may also be carried out by means of ultrasound.

A shaking of the container holder 5 and consequently of the sample in the sample container 8 received by the said container holder 5 may also be provided. For this purpose, expediently, the container holder 5 is suspended cardanically at its upper end and can be driven by an electric motor 9. During operation, the electric motor 9 drives a ball 10, located eccentrically on the shaft of the electric motor 9, at a controlled speed, the ball 10 being arranged in a central hollow journal 11 below the bottom of the container holder 5, and, via its eccentric arrangement, subjecting the container holder 5, on account of the cardanic suspension at its upper end, and, consequently, a sample container 8 located therein to a rotating pivoting movement.

The cardanic suspension may take place via a cambered ring 12 which is mounted on the stand 1 via two axes 13 arranged opposite one another at 180° and on which the container holder 5 is mounted via two further axes 13 offset at 90° thereto.

In order to ensure temperature conditions for sampling which are as identical as possible, it may be expedient to surround the container holder 5 with a thermal control device, for example in the form of a heating coil 14, and, if appropriate, with a cooling device, for example a cooling coil (not illustrated) through which coolant flows.

The sampler 2 carries a holder 15 comprising a vertical holding tube 16 which is inserted into an orifice 17 of the slide 2 and which is consequently open towards the respective sample container 8 and at the upper end. A reception tube 18 for a sample tube 33 is inserted into the holding tube 16, the reception tube 18 having arranged below it a spring 19 loading the latter in the upward direction, in the holding tube 16. The spring 19 is supported on an inwardly directed shoulder of the holding tube 16.

The holding tube 16 comprises a gas inlet connection 20 in the middle region. A gas outlet connection 21 is found in the reception tube 18 that extends from the upper region of tube 16. The sample tube 33 carries, at the end facing the container holder 5, an insert 22 which is inserted sealingly via O-rings and which carries a somewhat eccentrically arranged syringe needle 23, the inlet orifice of which is connected to an orifice (not illustrated) in the wall of the reception tube 18.

Located above the insert 22, in the reception tube 18, is a further insert 24 which carries a centrally running syringe needle 25 which extends through the insert 22 and the upper orifice of which is located inside the reception tube 18. Expediently, the insert 24 is sealed off via an O-ring 26 with respect to the inner wall of the reception tube 18. An additional conical spring 27 is arranged above the O-ring 26.

At the upper end of the holding tube 16, a latching device 28 for detaining the reception tube 18 in the extraction position is provided. The said latching device comprises at least two (opposite) or more (circumferentially distributed) sleeves 29 which in each case receive a piston 30 spring-loaded towards the inside of the tube 16 and having a latching surface 31 in the form of a spherical sector. The reception tube 18 receives captively at its upper end balls 32 which can latch into the latching surfaces 31.

To receive a sample to be analyzed by means of an analyzer, for example a gas chromatograph, sample tubes 33 are provided which are open on both sides and can be inserted into the reception tube 18 and which contain a, for example, porous packing 34 with adsorbing and/or sorbing material for the analytes to be analyzed. In this case, the packing 34 is held by a narrowing 35 of the sample tube 33. Seated on the sample tube 33 is a transporting head 36 which in a tapering portion carries two O-rings 37 which are spaced apart from one another and by means of which it can be inserted sealingly into the reception tube 18. An inlet bore 38 leading outwards opens out between the O-rings 37. Moreover, the transporting head 36 comprises a shoulder 39, against which the balls 32 can come to lie.

After the insertion of the sample tube 33 and its transporting head 36 into the reception tube 18 according to FIG. 1, the latter can be pressed via the transporting head 36 downwards in the direction of the sample container 8 counter to the force of the spring 19, until the balls 32 latch in the latching surfaces 31 of the pistons 30 which, for this purpose, may expediently have a chamfered edge, FIG. 2. As a result, at the same time, the transporting head 36 is pressed by the balls 32 into a sealing fit into the reception tube 18. The inlet bore 38 and consequently the interior of the sample tube 33 are thereby at the same time connected to the gas outlet connection 21.

Moreover, due to the downward movement, the septum 6 of the sample container 8 is pierced by the two syringe needles 23, 25 and, furthermore, the syringe needle 23 is connected to the gas inlet connection 20.

Sampling can then take place, in that inert gas from an inert-gas source is induced to flow via the gas inlet connection 20 into the syringe needle 23 and from there into the sample container 8, after which the laden inert gas is led through the syringe needle 25 into the sample tube 33 through the packing 34 for taking up the analytes and out of the sample tube 33 via the inlet bore 38 and the gas outlet connection 21.

The holding tube 16 and, if appropriate, a supply line, not illustrated, for inert gas may also be thermally controlled by means of heating, not illustrated, and/or for cooling (Peltier element 40 and fan 41), in order to ensure a uniform temperature everywhere and consequently also to ensure a standardized gas flow.

In the sampling positions, whether these serve momentarily as a preparation position or an extraction position, the sample container 8 can be shaken by the movement of the container holder 5. The cardanic suspension of the container holder 5 leads to extremely low load between the syringe needles 23, 25 and the septum 6. If appropriate, as already stated above, the sample may also be intermixed differently.

Whereas, in one sampling position, the sample there is conditioned to prepare it for extraction, in the other sampling position the sampling of the already conditioned sample located there is performed by means of the sampler 2 which subsequently moves into the other sampling position in order to commence sampling there. In this case, identical conditioning and extraction times, where conditioning and extraction times may be different, can always be implemented for series of samples.

If appropriate, an additional neutral position may also be provided for the sampler 2, in which case one position is used only as the preparation position and the other only as the extraction position, and the respective sample container 8 is transferred out of the preparation position into the extraction position after conditioning.

After sampling, the sample tube 33 can be removed by means of a gripper engaging on its transporting head 36 and can be inserted, for example, into a thermodesorption device of an analyzer for the purpose of analysis.

A handling device 44, comprising a gripper which is movable in three axes perpendicular to one another and by means of which the sample tube 33 provided with a transporting head 36 can be handled, is described in DE 102 19 790 C1. In this case, even sample containers 8 with a magnetizable cap 7 can be handled if the gripper of the handling device 44 is designed for holding the sample container 8 or is provided for this purpose, for example, with inserted permanent magnets which can hold the sample container 8 via its magnetizable cap 7.

The procedure is then as follows:

A sample container 8 is taken out from a magazine for sample containers 8 by means of the handling device 44 and is inserted into the container holder 5 in the sampling position which is to be used momentarily as a preparation position. The sample located in the sample container 8 is thermally controlled and/or shaken there.

The sampler 2 is moved (or pivoted, if it is arranged on a pivoting arm instead of on a slide) over the sample container 8 having the sample prepared for extraction.

Here, or even before movement, a sample tube 33 provided with a packing 34 and carrying a transporting head 36 is taken out from a magazine for sample tubes 33 by means of the handling device and is inserted into the reception tube 18. The lower end of the sample tube 33 is seated on the O-ring 26. However, in the position above the sample container 8, with the sample prepared for extraction, the sample tube 33 and consequently the reception tube 18 are pressed downwards counter to the force of the spring 19 by means of the handling device 44, until the said reception tube 18 latches in the holding tube 16 and is consequently detained. The needles 23, 25 have then pierced the septum 6 of the sample container 8, the needle 25 projects with its upper end into the inserted sample tube 33, and the gas inlet and gas discharge conditions are provided.

An inert-gas stream is then led from an inert-gas source via the needle 23 through the sample container 8, the needle 25 and the packing 34 in the sample tube 33, in order to extract sample material from the sample contained in the sample container 8 and transfer it to the packing 34.

Thereafter, by means of the handling device 44, the sample tube 33, together with the packing 34 laden with analytes, is first drawn up via the transporting head 36 together with the reception tube 18, with the detention of the latter being released. After the release of the detention, the spring 19 pushes the reception tube 18 upwards into its initial position of FIG. 1. At the same time, due to the release of the detention, the pressure exerted by the balls 32 on the adjacent shoulder 39 of the transporting head 36 is also eliminated, so that, with initial assistance by the spring 27, the sample tube 33 can be drawn out of the reception tube 18.

The sampler 2 is subsequently moved back into the other sampling position, in which, in the meantime, a further sample has been (or is being) conditioned, in order, after the conclusion of conditioning, to carry out sampling there using a new sample tube 33.

The respective sample tube 33, together with the laden packing 34, may, if appropriate, after intermediate storage in a magazine with the sample thus far prepared for analysis, be transported, for example, to a thermodesorption device of an analyzer by means of the handling device 44.

Instead of a packing 34 inserted separately into the sample tube 33, the said packing may also be formed by a corresponding inner coating of the sample tube 33.

Figure 4:
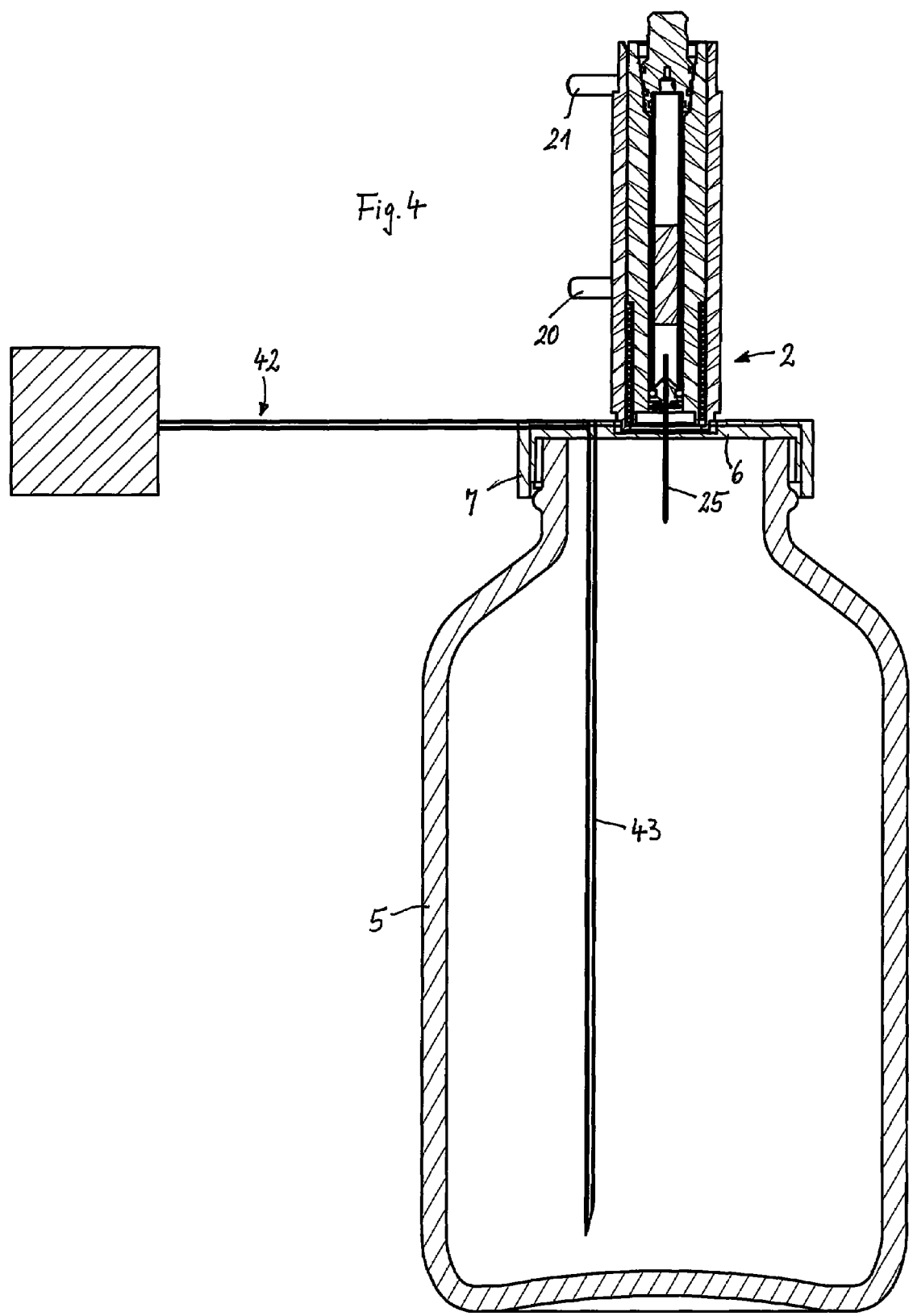
FIG. 4 shows in cross-sectional view a special sample container with an attached sampler which is illustrated diagrammatically.

If sample containers 8 of very large volume, for example liter containers, are used instead of conventional vials, it may be advantageous to provide, instead of or in addition to the gas supply via the syringe needle 23, a separate gas supply 42 which comprises a tube 43 leading almost as far as the bottom of the sample container 8, so that the inert gas supplied thereby can virtually flush through the entire container height, cf. FIG. 4.

Figure 5:
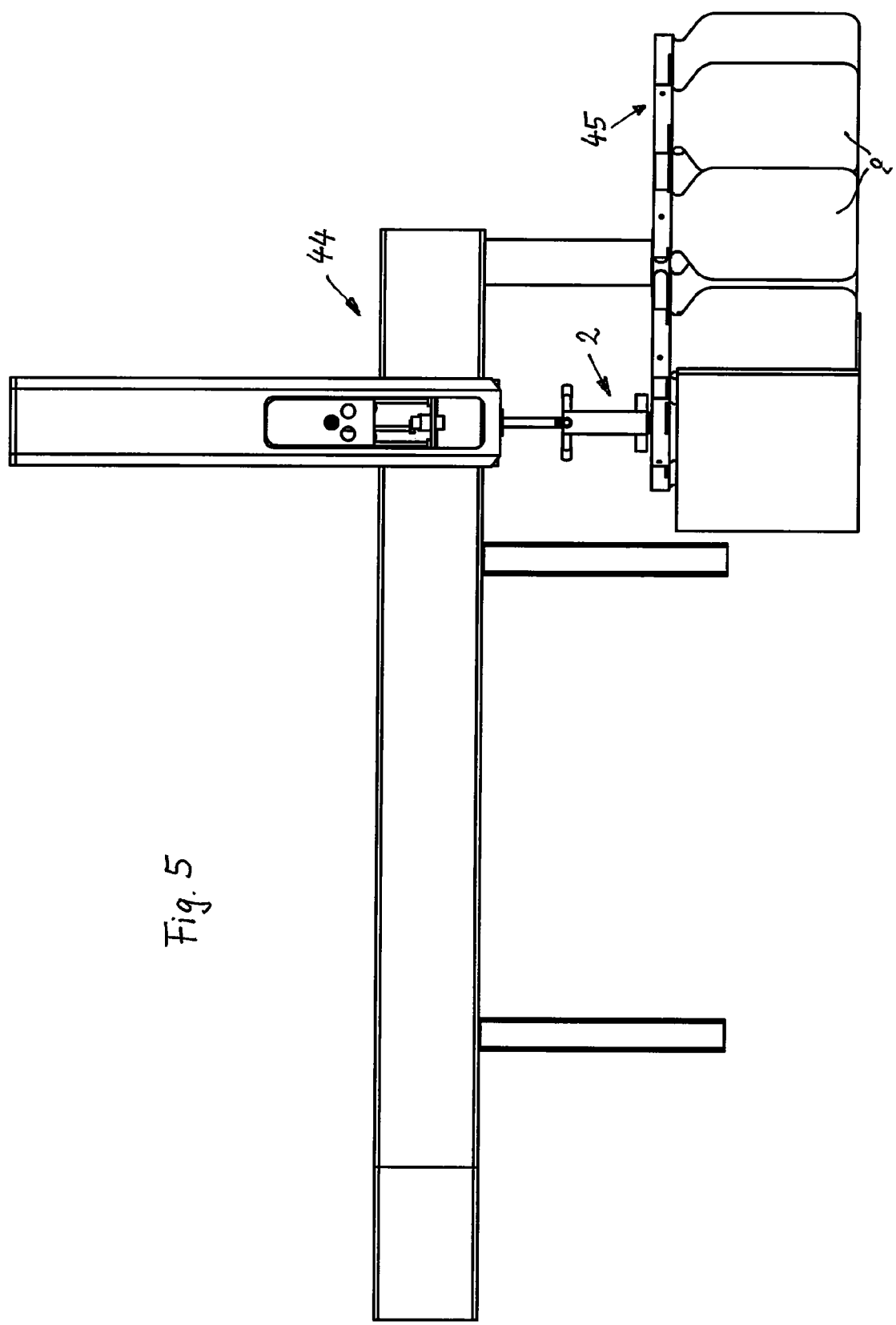
FIGS. 5 and 6 show diagrammatically a handling device and a sampling station.
Figure 6:
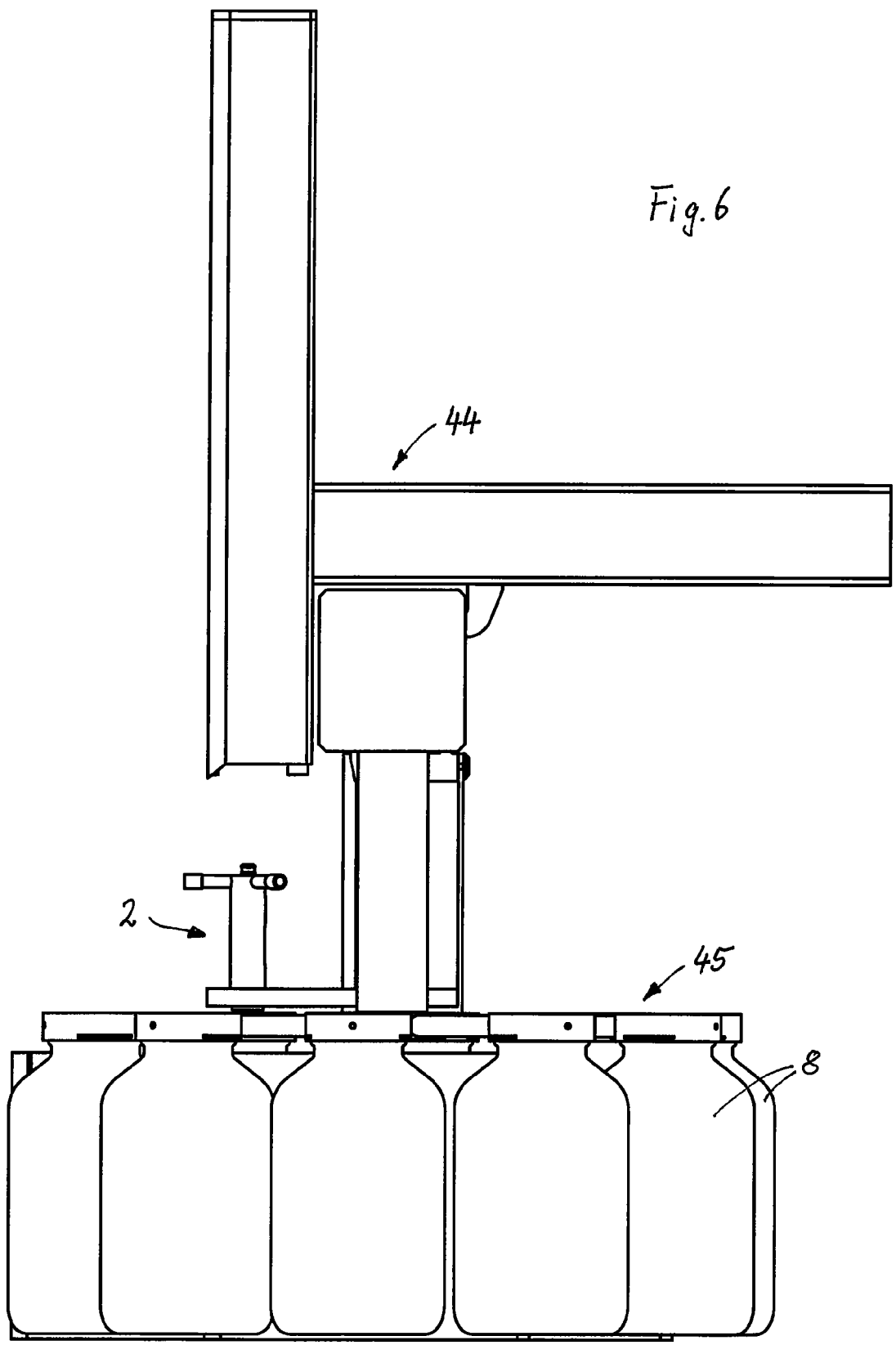

Since sample containers 8 of such large size, as illustrated in FIG. 4, cannot be handled by means of a handling device 44 for vials and sample tubes 33, it is in this case expedient to arrange the sample containers 8 on a turntable 45 which rotates the sample container 8 required in each case into the extraction position, so that a sample can be extracted by means of the sampler 2 then arranged above it, cf. FIGS. 5 and 6.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for the preparation of samples for an analyzer whereby
    a sample container provided with a septum is brought into an extraction position of a sampling station comprising a sampler,
    the sampler is arranged in an extraction position above the sample container, the sampler comprising, a sample tube, a reception tube movable in the direction of the sample container and detainable in an end position in a holder, and a syringe needle, which terminates in the reception tube, being movable by means of the reception tube,
    the sample tube open on both sides, in which there is a packing for the uptake of analytes is inserted into the reception tube and, together with the latter, is moved within the holder in the direction of the sample container and detained, with the septum being pierced by the needle,
    an inert-gas stream is led from an inert-gas source through the sample container, the needle and the packing in the sample tube, and
    the sample tube, together with the packing laden with analytes, is removed from the reception tube.

2. The method according to claim 1, wherein the inert-gas stream is led via a further syringe needle, co-movable with the reception tube, into the sample container.

3. The method according to claim 1, wherein the inert-gas stream is led via a separate gas supply as far as the bottom of the sample container.

4. The method according to claim 1, wherein the inert gas introduced into the sample tube via the syringe needle is discharged via a transporting head located on the sample tube and capable of being handled by a handling device.

5. The method according to claim 1, wherein the sample container is thermally controlled before and/or during the sampling.

6. The method according to claim 1, wherein the sample is intermixed before and/or during the sampling.

7. The method according to claim 6, wherein the sample container is shaken.

8. The method according to claim 1, wherein a sample contained in a sample container is prepared for sampling in one position and extraction is carried out in the other position.

9. A sampling station for the preparation of samples for an analyzer from a sample container provided with a septum, comprising
    a container holder, arranged in an extraction position, for a removable sample container, wherein the container holder can be individually thermally controlled, and
    a sampler with a holder, movable over the sample container in the extraction position, for a reception tube for a sample tube open on both sides, with a packing for the uptake of analytes,
    the reception tube being introducible and detainable in the holder and carrying a taken-along syringe needle which opens out inside the reception tube so as to project out of the latter.

10. The sampling station according to claim 9, wherein the sampler is movable in a slide-like manner with respect to the container holder.

11. The sampling station according to claim 9, wherein the reception tube can be pressed into its holder and detained counter to a spring.

12. The sampling station according to claim 11, wherein a further syringe needle taken along by the reception tube is, with the reception tube detained in its holder, fluid-connected to an inert-gas supply in the holder.

13. The sampling station according to claim 9, wherein the reception tube carries at least one ball which can be brought into latching engagement with a piston, spring-prestressed in the direction of the reception tube, of the holder for the reception tube.

14. The sampling station according to claim 13, wherein the sample tube can be pressed into the reception tube by means of the latched ball.

15. The sampling station according to claim 13, wherein the sample tube can be pressed into the reception tube by means of a transporting head located thereon.

16. The sampling station according to claim 15, wherein the transporting head for the sample tube can be pressed into sealing engagement with the reception tube.

17. The sampling station according to claim 15, wherein the transporting head comprises an inlet bore for an inert-gas discharge.

18. The sampling station according to claim 17, wherein the sampler can be individually thermally controlled.

19. The sampling station according to claim 9, wherein a further container holder is arranged in a preparation position.

20. The sampling station according to claim 9, wherein the sample is intermiscible.

21. The sampling station according to claim 20, wherein the container holder is shakable while in one of the sampling position, the preparation position and the extraction position.

22. The sampling station according to claim 21, wherein the container holder is suspended cardanically at its upper end and on its underside has an eccentric drive.

* * * * *